United States Patent [19]

Smiley et al.

[11] Patent Number: 4,457,707

[45] Date of Patent: * Jul. 3, 1984

[54] INTEGRATED ORAL MAGNETIC OSTEOGENIC AND ORTHODONTIC APPLIANCES

[75] Inventors: Harry Smiley, White Plains; Abraham Blechman, Tappan, both of N.Y.

[73] Assignee: Medical Magnetics, Inc., Ramsey, N.J.

[*] Notice: The portion of the term of this patent subsequent to Jan. 3, 2001 has been disclaimed.

[21] Appl. No.: 516,201

[22] Filed: Jul. 22, 1983

Related U.S. Application Data

[63] Continuation-in-part of Ser. No. 322,423, Nov. 18, 1981, Pat. No. 4,424,030, which is a continuation of Ser. No. 19,427, Mar. 12, 1979, abandoned.

[51] Int. Cl.³ .............................................. A61C 7/00
[52] U.S. Cl. ..................................................... 433/18
[58] Field of Search ................................. 433/18, 189

[56] References Cited

U.S. PATENT DOCUMENTS

| 3,353,271 | 11/1967 | Blechman | 433/18 |
| 3,646,676 | 3/1972 | Mitchell | 433/189 |
| 3,984,915 | 10/1976 | Noble | 433/18 |
| 4,017,973 | 4/1977 | Nelson | 433/18 |

Primary Examiner—Robert Peshock
Attorney, Agent, or Firm—Hopgood, Calimafde, Kalil, Blaustein & Judlowe

[57] ABSTRACT

Various types of magnetic or electromagnetic appliances attached intra-orally or extra-orally are used to produce osteogenesis and soft tissue repair in the practice of periodontics and orthodontics. Simultaneously, these innovative magnetic modules generate force fields that produce corrective tooth movement.

6 Claims, 12 Drawing Figures

INTEGRATED ORAL MAGNETIC OSTEOGENIC AND ORTHODONTIC APPLIANCES

RELATED CASE

This application is a continuation-in-part of our co-pending application, Ser. No. 06/322,423, filed Nov. 18, 1981 now Pat. No. 4,424,030 issued Jan. 03, 1984, and said copending application is a continuation of our co-pending application Ser. No. 019,427, filed Mar. 12, 1979 (now abandoned).

BRIEF SUMMARY OF THE INVENTION AND DRAWINGS

This invention relates to the use of magnetic modules in the corrective treatment of dental misalignments and disease.

The invention represents a total departure from existing dental devices in that it produces soft-tissue repair and osteogenesis in the upper and lower jaws, accomplished by affixing permanent magnets, electromagnets or electromagnetic induction coils to the teeth, archwires and other suitable devices which create a regenerative current. The extremely low frequency magnetic field produced by mandibular movement in conjunction with its interaction with adjacent internal electrolytes is a source of this regenerative current. These procedures have application in enhancing therapy in periodontics and orthodontics. This is a new and useful therapeutic modality, in that it is totally non-invasive as opposed to the present method of treatment of this common disease by surgical intervention.

Concomitantly, these new devices can be used to produce force fields which will induce orthodontic movement when necessary. This latter object is an improvement over the prior art in that it possesses the following advantages:

1. Intermaxillary and intramaxillary force applications are not dependent on patient cooperation. All forces are determined and controlled by the operator.

2. Totally independent mounting of any type of standard orthodontic applicance in use, possessing greater flexibility and eliminating interference.

3. Insures the maximum effect of a continuous force field which has heretofore been an unattainable optimal condition necessary for tooth movement by preventing buccal torquing of the magnetic sleeve module.

4. Bio-compatible sleeve to enclose and protect the magnet.

5. Rectangular orthodontic tube or alternate geometric configurations which will resist buccal torquing of the entire magnetic sleeve module is soldered or otherwise suitably connected to the lingual aspect of the sleeve.

6. When needed or desirable, proper preparation of the magnets will induce torquing of one magnet when its attractive pole is brought into contact with another magnet. These magnets mounted in accordance with this principle, in this invention, are used in orthodontic therapy where torquing of the teeth is required.

7. For the first time in orthodontic therapy, this invention makes possible the use of a force that increases in value as time progresses, i.e., as the magnetic poles approach each other. Safer physiologic responses, fewer and painless orthodontic adjustments, and drastically decreased treatment time are attributed to this unique quality of the force.

8. All other orthodontic force systems when used in an intermaxillary mode demonstrate large vertical force vectors which tend to unseat bands and increase the cant of the occlusal plane, leading to relapse of treatment. In contrast, with the invention, magnetic intermaxillary forces are essentially horizontal, thus providing a desirable response, hitherto unattainable with conventional forces and techniques.

9. This invention provides for alternate configurations of the magnets and involves a totally new approach in orthodontics, in that it utilizes magnets with fields so oriented that, when their attractive poles are not perfectly aligned in contact, a sliding or shearing force is produced with a minimal air gap between the poles. When reversed and used in repulsion, intrusion and cross-bite correction may be accomplished singly or in combination; in combination, this is the first time ever possible.

10. The flexibility inherent in this invention is not limited to magnetic materials in current use, but may easily be adapted to materials now unknown which develop the suitable properties required. Further, there are innumerable variations including sizes, amounts, shapes of magnets and the electromagnetic and force fields generated, as well as functional or removable appliances (within the mouth or outside) which may carry at least one magnet to develop an attracting or repulsive force, as needed.

These advantages will hereinafter be amplified and become more apparent in the data provided in the construction and operation as more fully subsequently described and claimed, reference being had to the annexed drawings forming a part hereof, wherein like numerals refer to like parts throughout, and in which:

Figure 5:
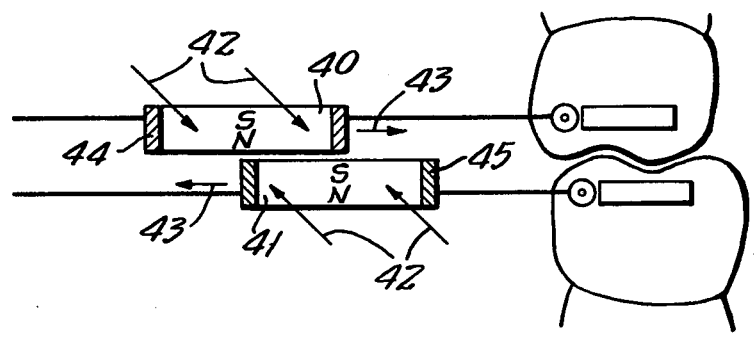
FIG. 5 is a lateral view of a magnetic orthodontic appliance mounted on a portion of the dentition of the upper and lower jaw of a human being, to demonstrate desirable attraction-force fields through shearing with a minimal air gap.
Figure 7:
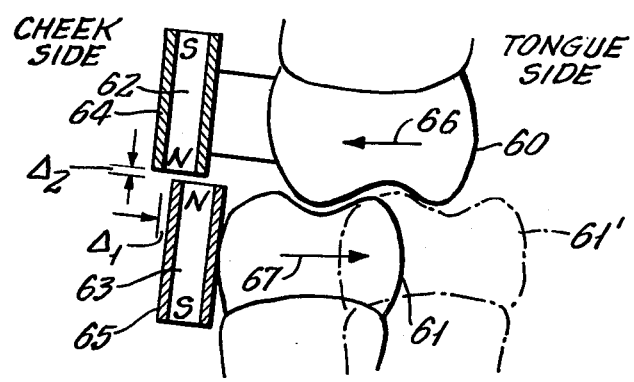
Figure 8:
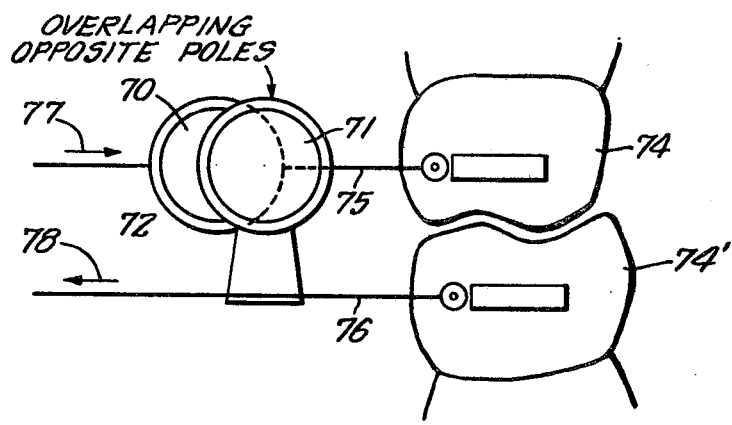
Figure 9:
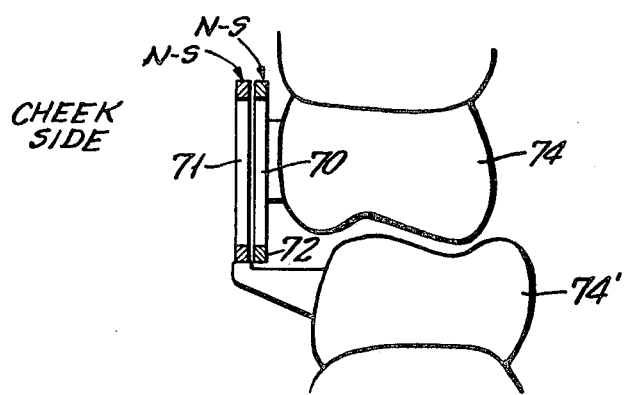
Figure 10:
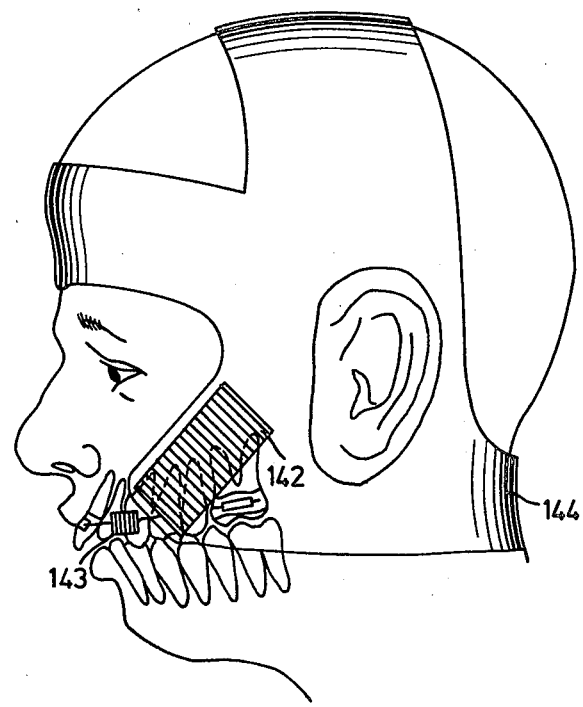
Figure 11:
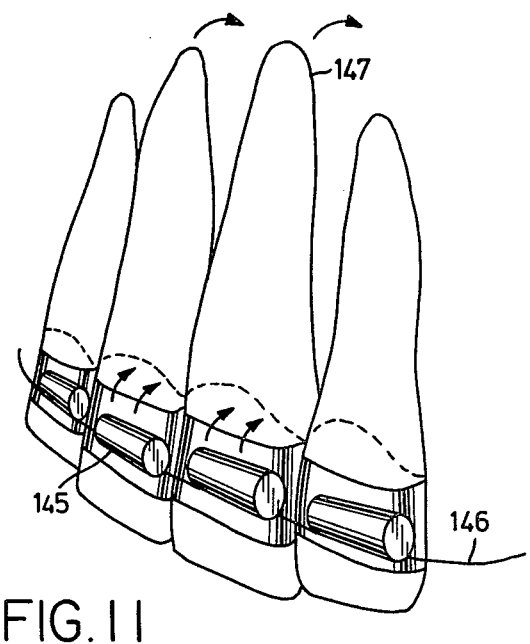
Figure 12:
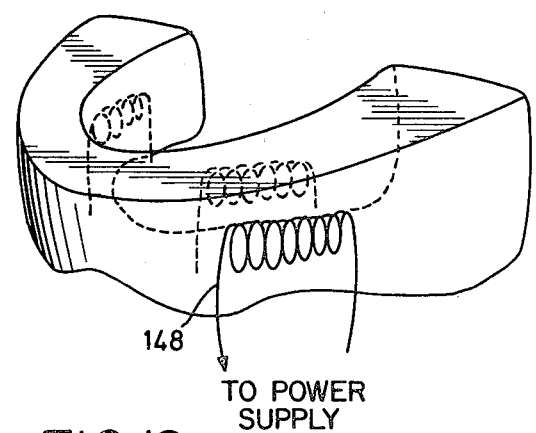

FIG. 7 demonstrates use of the invention for crossbite correction;

FIG. 8 is a view from the aspect of FIG. 5, to illustrate another embodiment;

FIG. 9 is a view from the aspect of FIG. 7 but applicable to the embodiment of FIG. 8;

FIG. 10 is a left lateral view of extra-orally mounted magnets operating with intra-orally mounted magnets on an orthodontic appliance;

FIG. 11 is a simplified perspective perspective view to demonstrate the torquing effect of magnets on anterior teeth; and FIG. 12 is a perspective view of induction coils mounted in an intra-oral device for use in periodontal therapy.

DETAILED DESCRIPTION OF DRAWINGS

Figure 1:
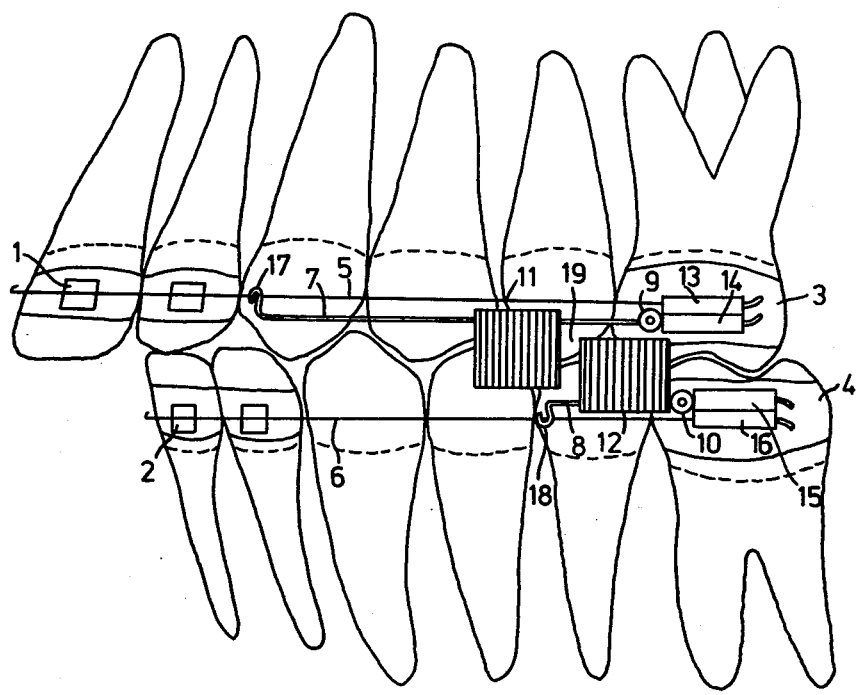
FIG. 1 is a lateral view of an integrated oral magnetic osteogenic and orthodontic appliance mounted on a portion of the dentition of the upper and lower jaw of a human being, with a class II malocclusion.

FIG. 1 of the drawings shows an orthodontic appliance mounted on a portion of the dentition of the upper and lower jaw of a human being, with a Class II malocclusion. The orthodontic appliance includes upper anterior bands 1 mounted to the anterior teeth and having wire-securing brackets thereon, an upper posterior band 3 mounted to an upper rear molar and having a maxillary superior molar tube 13 mounted thereon, and an upper-base archwire 5 connecting the brackets on the anterior bands 1 and the molar tube 13 on the posterior band. The bands and brackets are shown and described in more detail in Blechman Pat. No. 3,353,271, issued Nov. 21, 1967. Lower anterior bands 2 with suitable wire mounting brackets thereon are connected by a lower-base archwire 6 to a mandibular inferior molar tube 16 mounted on a lower molar band 4.

An upper sectional archwire 7 independent of the main-base archwire 5 is connected at one end to a maxillary inferior molar tube 14 mounted on the molar band 3 and at its other end by a hook extension 17 to the archwire 5. The archwire 7 serves as a support for a magnetic module 11. The magnetic module 11 includes a magnet accommodated within a sleeve. A lock 9 attached to the archwire 7 and intermediate the module 11 and the molar tube 14 permits fore-and-aft adjustment of the magnetic module 11.

A lower archwire 8 independent of the archwire 6 supports a magnetic module 12 thereon. The archwire 8 is connected at one end to a mandibular superior molar tube 15 mounted on the band 4 and at the other end by a hook extension 18 of the archwire 8 to the archwire 6. A lock 10 attached to the lower archwire 8 intermediate the module 12 and the molar tube 15 permits fore-and-aft adjustment of the magnetic module 12.

The magnetic modules 11 and 12 are spaced apart end-to-end to provide an air gap 19 between the attractive poles of the magnets. This air gap can be adjusted by moving the modules when required to requlate the magnetic force between them. The orientation of the magnetic modules 11 and 12 can also be adjusted relative to each other by bending the archwires 7 and 8 so that the poles of the magnet can be aligned.

The archwires 7 and 8 and the passages through the molar tubes 14 and 15 which anchor the archwires 7 and 8 are preferably of rectangular cross section, for example, 0.022"×0.028" to prevent buccal torquing of the magnetic of the magnetic modules when the archwires 7 and 8 are inserted therein, thereby permitting the poles of the magnetic modules 11 and 12 to remain properly aligned at all times so that continuous orthodontic movement will be accomplished.

The integrated oral magnetic osteogenic and orthodontic appliance shown in FIG. 1 creates a magnetic field in the adjacent bony tissue so that mandibular movement during mastication, speech, etc. generates a low frequency changing electromagnetic field around and near both magnets; this varying field interacts with body cells and/or tissues, and with circulating vascular and inter-cellular electrolytes. Simultaneous orthodontic movement is imparted to the teeth by the magnetic force field. Normally, during tooth movement, osteoclastic activity of the alveolar bone is induced, and subsequently osteogenesis must occur to insure successful orthodontic treatment. This invention accelerates the rate of osteogenesis and also stimulates osteogenesis in areas where this is necessary but may not occur.

Tooth movement accelerated by the continuous application of force plus increased osteogenic activity accelerates treatment time. In addition, stimulation of osteogenesis in areas where this should occur but fails to occur prevents subsequent periodontal disease and possible early loss of teeth. Thus, this appliance can be utilized in the treatment of periodontal disease even where orthodontic requirements are not necessary.

Figure 2:
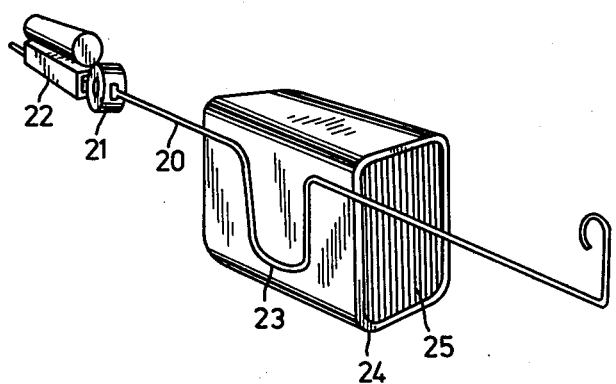
FIG. 2 is a lingual view in perspective of one of the components of the appliance in FIG. 1.

FIG. 2 is a more detailed view of one of the magnetic modules 11 or 12 shown in FIG. 1. The magnetic module includes a permanent magnet 25 accommodated within a magnet holding sleeve 24. The sleeve 24 is non-magnetic and electrically conductive, and is preferably but not necessarily of a surgical grade stainless steel; sleeve 24 is mounted to an archwire having a hook extension at one end and a buccal tube 22 at the opposite end. The hook extension, as described above in connection with FIG. 1, is adapted to be mounted on another archwire, and the buccal tube 22 is adapted to be mounted on a molar band. An orthodontic lock 21 on the archwire 20 prevents the archwire from moving relative to the tube when properly locked in place, thereby directly transmitting the magnetic force to the molar tooth.

The archwire is of rectangular cross section and is received within a rectangular passage of generally complementary shape in the tube 22. A U-bend 23 in the archwire facilitates attachment of the archwire to the sleeve by soldering, welding or other suitable means.

The permanent magnet is anchored in the sleeve by a bio-compatible adhesive material, such as an acrylic, epoxy, urethane, or other suitable adhesive material. The exposed poles of the magnet are preferably coated with the adhesive material to prevent corrosion products from leaching into the oral cavity when SmCo, PtCo, AlNiCo, or other magnets are used.

Figure 3:
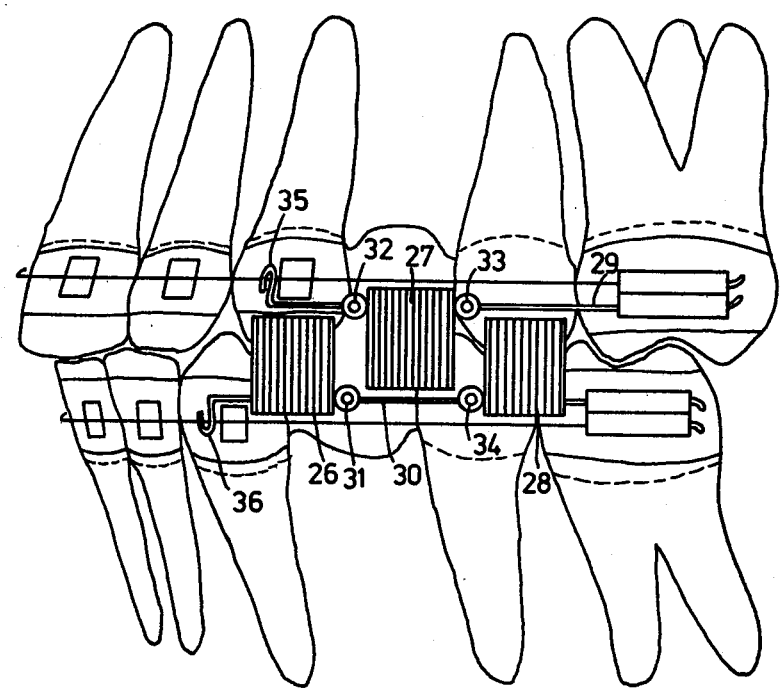
FIG. 3 is a lateral view of a magnetic orthodontic appliance mounted on a portion of the dentition of the upper and lower jaw of a human being, with Class 1 malocclusion requiring extractions.

FIG. 3 of the drawings shows an orthodontic appliance of the present invention mounted on a portion of the upper and lower jaw of a human being, with a Class I malocclusion requiring extractions. This appliance utilizes the basic mounting and independent archwires of the appliance described above in connection with FIG. 1.

More specifically, the orthodontic appliance shown in FIG. 3 utilizes three magnetic modules 26, 27 and 28, on each side of the mouth. The middle module 27 is mounted on an upper sectional archwire 29 intermediate a pair of orthodontic locks 32 and 33. The anterior end of the archwire 29 has a hook extension 35 bent to engage the main archwire immediately mesial to a bracket mounted to the upper cuspid to be moved distally. The anterior and posterior magnetic modules 26 and 28, respectively, are mounted to a lower archwire 30, mounted at its posterior end to a lower molar and having a hook extension 36 at its anterior end bent to engage the main archwire immediately mesial to a bracket attached to the lower cuspid to be moved distally. An orthodontic lock 31 is mounted on the archwire 30 distal to the module 26, and an orthodontic lock 34 is mounted on the archwire 30 mesial to the magnetic module 28. The orthodontic locks are provided to lock the modules to the archwires, but they can be released to adjust the positions of the modules and the size of the air gaps.

The modules are arranged so that distal movement of the upper and lower cuspid teeth can be accomplished simultaneously. Toward this end, the poles of the magnets are positioned so that the middle module 27 is attracted to the posterior lower module 28 to move the upper cuspid distally. At the same time, the anterior lower module 26 is attracted to the middle module 27 to move the lower cuspid distally. Concomitantly, osteogenesis is induced in the adjacent alveolar bone by mandibular movement.

Figure 4:
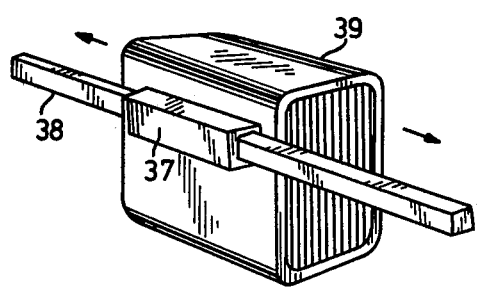
FIG. 4 is a view similar to FIG. 2, to show a modification, usable in the appliances of FIGS. 1 and 3.

As shown in FIG. 4 of the drawings, the magnetic module can be provided with a mounting means 37 to facilitate its adjustment on an archwire for adjustment of the air gap between poles of the magnets. The mounting means 37 shown in FIG. 4 is an elongate tube carried by the sleeve 39 to permit the module to be adjusted relative to a supporting archwire 38; tube 37 may be mounted anywhere on the sleeve to facilitate particular treatment. The archwire and the passage through the tubular mounting means are of complementary shape, for example, rectangular in cross section, to prevent torquing or twisting of the module on the wire while permitting the module to slide freely along the wire for adjustment. Tubes 37 of other geometric configuration (e.g., round or oval, and with or without a key slot or groove) may also be used, and properly bent archwires may be used to compensate for torquing. Magnets may be used in any repulsive, attractive or combination mode to generate the required vectors, and magnets may also be used in periodontal therapy, with shims at the air gap to limit force generation and to thus utilize to the full the osteogenic quality of the varying magnetic field.

FIG. 5 shows a magnetic orthodontic appliance mounted on a portion of the dentition of the upper and lower jaw of a human being, to illustrate desirable force fields through shearing with a minimal air gap. A maxillary magnetic module 40 and a mandibular magnetic module 41 are mounted on their respective supporting archwires and in attracting polarity relation so that resultant magnetic force vectors are oriented diagonally, as indicated by slanted arrows 42. Since the magnetic poles will tend to align, the shearing effect of the horizontal component of the resultant force produces desired orthodontic forces on the archwires, as indicated by the arrows 43. Sectional cross-hatching at 44–45 will be understood to show the conductive sleeve (corresponding to sleeve 24 in FIG. 1) around each of the respective magnets 40–41. The minimal air gap eliminates friction between the poles and simultaneously generates a maximal force. Concomitantly, osteogenesis and soft tissue repair are achieved by the low frequency varying magnetic field described above.

Figure 6:
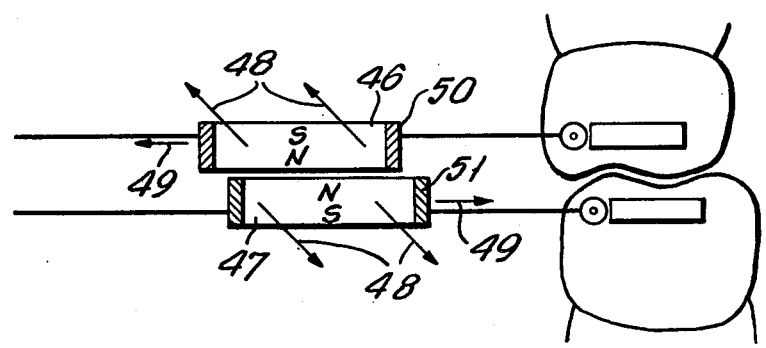
FIG. 6 is a view similar to FIG. 5 to illustrate a repulsion-force situation.

The arrangement of FIG. 6 will be seen to be very much the same as in FIG. 5, with the exception that the polarity relation of the magnets 46–47 is reversed, to place like poles in closely spaced adjacency but, again, at horizontal offset from each other. The resultant force vectors 48 are inclined but in the repulse direction, producing a horizontal component 49 of force reaction upon the upper and lower teeth to which the respective magnets are referenced. Conductive sheaths 50–51 again surround the respective magnets. The arrangement of FIG. 7 illustrates use of the invention in an orthodontic procedure wherein jaws which are initially at lateral offset are to be adjusted laterally to correct their alignment. The view of FIG. 7 will be understood to be taken at a transverse cut through one side of the jaws, to provide an elevational aspect on upper and lower molars 60–61, wherein the lower molar 61 on the cheek side is to be displaced from its solid-line or offset position, into its ultimately corrected tongue side position shown by dashed outline 61', using upper and lower permanent magnets 62–63, with conductive sheaths 64–65 as previously described, and oriented for mutual repulsion. The procedure for use of magnets 64–65 for the indicated purpose may involve resetting and adjusted reorientation of both magnets in the course of several weeks of periodic meetings with the patient, but for simplicity of explanation, it will be assumed that the entire procedure requires progressive adjustment of only the upper magnet 62 on its tooth (or multiple-tooth) reference mount, the other magnet 63 being in the same fixedly mounted relation to its tooth 61 (or plural adjacent teeth) throughout the procedure. The procedure will also be understood to be bilateral in its application, as will later be more fully explained.

For the initial condition of misalignment shown for teeth 60–61 in FIG. 7, the problem of effecting progressive displacement from initial position 61 to desired final position 61' involves that of providing strong repulsion in the direction of arrows 66–67. This is best achieved in the region $\Delta_1$ of lateral offset of like pole faces of magnets 64–65, while preserving a degree of lateral overlap of these pole faces, as shown. Also, the gap $\Delta_2$ between pole faces should be as small as possible. The problem also involves recognition of the fact that, in the course of effecting lateral displacement from 61 to 61', the patient's bite will become more limited as interference progresses between crests of the teeth 60–61.

In the foregoing circumstances, it is recommended initially to mount magnet 62 in the laterally offset relation $\Delta_1$ shown, and with pole faces in contact (or separated by a thin shim, such as a 0.001 or 0.002 inch foil) when the jaws are fully closed. As lateral displacement occurs, the lateral offset $\Delta_1$ increases (thus reducing pole-face overlap), and the teeth 60–61 interfere, causing gap $\Delta_2$ to increase, for the jaws-closed condition. Thus, at intervals, the position of magnet 62 on its mount will require readjustment, involving reduction of $\Delta_1$ to its initial small setting, and reduction of $\Delta_2$ to zero or near zero. Once the tooth (61) displacement passes the point of maximum interference with tooth 60, the successive readjustments of magnet 60 will require a larger shim (e.g., 0.005 to 0.010 inch foil) to determine a reset value of $\Delta_2$, to permit achievement of maximum jaw closure.

It has been indicated above that the procedure with respect to FIG. 7 is bilateral, to effect the indicated corrective displacement. By this it is meant that, in application to a jaw correction, another pair of magnets (not shown) will have been mounted to the cheek side of the corresponding molars at the other side of the mouth, and that repulse action should be used between the magnets of this other pair; the magnets should be mounted and adjusted as described for magnets 62–63, except that the direction of lateral-force development should of course be in the direction aiding the force 66–67 developed by reaction between magnets 62–63.

FIGS. 8 and 9 illustrate an embodiment of the invention wherein permanent magnets 70–71 are relatively thin discs and wherein the conductive sheath is a circumferential ring 72 (73) around each magnet 70 (71), the opposite faces of each magnet being oppositely polarized. Assuming that it is desired to force an upper tooth 74 rearward with respect to a corresponding lower tooth 74', the discs 70 (71) are so mounted to archwires 75 (76) referenced to the respective teeth, and the polarity orientation of the partially overlapping discs is so selected that, for the jaw-closed condition, the adjacent poles of the magnetized discs react in the directions shown by arrows 77 (78). For the arrangement shown, opposite poles are adjacent, so that the magnets seek a greater degree of overlapping registration, as seen from the aspect of FIG. 8. As seen in FIG. 9, the discs 70-71 are in close laterally spaced relation, primarily at the elevation of the upper-jaw tooth 74, and are both on the cheek side of the tooth. For the closed condition of the mouth, there is constant application of force in the direction of arrows 77 (78); and when the jaws are opened and closed, the forces become intensity-modulated in the direction of arrows 77 (78), while the magnetic flux in the tooth and gum region adjacent the upper magnet 70 is subjected to relatively great excursions of intensity, by reason of jaw articulation, thus accounting for induced therapeutically beneficial currents in body cells within the involved region.

It is found that orthodontic correctional procedures are very materially aided by the invention. This is believed to be attributable to the fact that the reacting magnets are always acting; they are always acting with greatest force for the jaw-closed condition; and the greatest change in magnetic flux development also occurs at and near the jaw-closed condition, for greatest coupling to body cells and/or tissues, and therefore of greatest osteogenic effect when the orthodontic correction force is at or near maximum.

In FIG. 10, an intra-oral magnetic module 143 mounted on an orthodontic appliance is adapted to cooperate with an extra-oral magnet 142 mounted in or affixed to headgear 144 worn by the patient. There is no physical contact between the extra-oral magnet and the intra-oral magnetic module. Magnetic force fields are generated through the cheek without sensation to the patient. The arrangement shown in FIG. 10 illustrates a high pull arrangement. However, the extra-oral magnet can be mounted to produce high, medium or low pulling forces, as required. The arrangement shown in FIG. 6 requires patient cooperation.

FIG. 11 illustrates an orthodontic technique for imparting a torquing effect on the anterior teeth 147. An orthodontic archwire 146, suitably mounted to extend across the lower regions of the anterior teeth, supports a plurality of magnetic modules 145 thereon, with their respective axes arranged so as to impart the desired twisting or torquing action. For example, the magnetic modules can be attached to orthodontic bands on their labial aspect in conjunction with the archwire which can be ligated to the modules. The resultant magnetic torquing is imparted to the teeth, causing lingual root torque, as illustrated by the arrows.

An intra-oral device embodying induction coils 148 mounted therein for use in periodontal therapy is illustrated in FIG. 12. The intra-oral device is custom-made for each individual patient and is constructed to fit the teeth of the upper and lower jaws, as required.

What is claimed is:

1. An oral osteogenic and orthodontic appliance in which at least two magnets are adapted to be mounted by archwires to the upper and lower jaws so that magnetic fields will be displaced relative to each other to promote osteogenesis and soft-tissue repair, said appliance including at least two dental modules, each module comprising a permanent bar magnet retained within a peripherally continuous shield of electrically conductive material so as to expose the magnet only at its poles, whereby flux concentration on the magnet axis is enhanced at the poles of each magnet, tooth-connected maxillary and mandibular archwires for supporting the dental modules, one module-supporting archwire supporting a first module on a vertically oriented axis and the other module-supporting archwire supporting the other module on a vertically oriented axis, the lower pole of the upper module magnet and the upper pole of the lower module magnet being in substantially opposed and closely spaced but axially offset adjacency for the jaw-closed condition; whereby, reaction between said magnets develops a tooth-displacement force effective to displace at least one tooth in one of the jaws and to thereby develop a void in the one jaw in the wake of such tooth displacement, and further whereby, in the course of jaw articulation, the magnetic fields of said magnets react to produce in the developing-void region an external field which varies as a function of jaw articulation, said external field being therapeutically beneficial as an aid to formation of new bone in the void region.

2. The appliance of claim 1, in which said adjacent poles are in partial overlap and are of like polarity.

3. The appliance of claim 1, in which said poles are in partial overlap and are of opposite polarity.

4. An oral osteogenic and orthodontic appliance in which at least two magnets are adapted to be mounted to the upper and lower jaws so that magnetic fields will be displaced relative to each other to promote osteogenesis and soft-tissue repair, said appliance including at least two dental modules, each module comprising a permanent disc magnet with its faces oppositely polarized and retained within a peripherally continuous shield of electrically conductive material so as to expose the magnet only at polarized faces, whereby flux concentration on the magnet axis is enhanced at the polarized faces of each magnet, first tooth-connected means of the upper jaw supporting a first module on an axis oriented horizontally between the cheek side and the tongue side of the region of the connected tooth, and second tooth-connected means of the upper jaw supporting a second module on an axis oriented horizontally between the cheek side and the tongue side of the region of the connected lower-jaw tooth, the modules having adjacent polarized faces in closely spaced but axially offset adjacency for the jaw-closed condition, the orientation of said offset being generally horizontal and placing the axis of one of said modules in anterior relation to the other of said modules for the jaw-closed condition; whereby reaction between said magnets develops a tooth-displacement force effective to displace at least one tooth in one of the jaws and to thereby develop a void in the one jaw in the wake of such tooth displacement, and further whereby, in the course of jaw articulation, the magnetic fields of said magnets react to produce in the developing-void region an external field which varies as a function of jaw articulation, said external field being therapeutically beneficial as an aid to formation of new bone in the void region.

5. The appliance of claim 4, in which the adjacent polarized faces are in substantial but less than total overlap and are of like polarity.

6. The appliance of claim 4, in which the adjacent polarized faces are in substantial but less than total overlap and are of opposite polarity.

* * * * *